(12) United States Patent
Julis et al.

(10) Patent No.: US 9,670,109 B2
(45) Date of Patent: Jun. 6, 2017

(54) METATHESIS REACTIONS WITH CARDANOL AND/OR ANACARDIC ACID

(71) Applicant: University Court of the University of St. Andrews, St. Andrews (GB)

(72) Inventors: Jennifer Julis, Dusseldorf (DE); David John Cole-Hamilton, Fife (GB); Catherine Cazin, Fife (GB)

(73) Assignee: University Court of the University of St. Andrews, St. Andrews (GB)

( * ) Notice: Subject to any disclaimer, the term of this patent is extended or adjusted under 35 U.S.C. 154(b) by 0 days.

(21) Appl. No.: 14/428,013

(22) PCT Filed: Sep. 11, 2013

(86) PCT No.: PCT/GB2013/052371
§ 371 (c)(1),
(2) Date: Mar. 13, 2015

(87) PCT Pub. No.: WO2014/041344
PCT Pub. Date: Mar. 20, 2014

(65) Prior Publication Data
US 2015/0321981 A1 Nov. 12, 2015

(30) Foreign Application Priority Data

Sep. 14, 2012 (GB) .................................. 1216463.8
Sep. 14, 2012 (GB) .................................. 1216491.9

(51) Int. Cl.
| C07C 37/50 | (2006.01) |
| C07C 41/03 | (2006.01) |
| C07C 1/20  | (2006.01) |
| C07C 37/00 | (2006.01) |
| C07C 39/19 | (2006.01) |

(52) U.S. Cl.
CPC .............. *C07C 1/20* (2013.01); *C07C 37/003* (2013.01); *C07C 37/50* (2013.01); *C07C 39/19* (2013.01); *C07C 41/03* (2013.01); C07C 2531/22 (2013.01); C07C 2531/28 (2013.01); Y02P 30/42 (2015.11)

(58) Field of Classification Search
None
See application file for complete search history.

(56) References Cited

U.S. PATENT DOCUMENTS

| 6,159,890 A | 12/2000 | Nubel et al. |
| 2006/0211905 A1 | 9/2006 | Forman et al. |

FOREIGN PATENT DOCUMENTS

| WO | WO01/46096 | 6/2001 |
| WO | WO2007/010453 | 1/2007 |

OTHER PUBLICATIONS

Dragutan et al. ("Ruthenium Indenylidene Complexes", Platinum Metals Rev, 2005, vol. 49, (1), pp. 33-40).*
Schwab, Peter et al., A Series of Well-Defined Metathesis Catalysts—Synthesis of [RuCl2(=CHR')(PR3)2] and Its Reactions, Angew. Chem. Int. Ed. Engle. 1995, 34, No. 18, pp. 2039-2041.
Boeda, Fabien et al., Ruthenium-indenylidene complexes: powerfule tools for metathesis transformations, Chem. Commun, 2008, pp. 2726-2740.
Cole-Hamilton, David, Catalytic Production of Chemicals from Waste Natural Oils, EaStCHEM, University of St,. Andrews, 64 pages, Sep. 16, 2012.
Nubel, P.O. et al., A convenient catalyst system employing RuCl3 or RuBr3 for metathesis of acyclic olefins, Journal of Molecular Catalysis A: Chemical 145 (1999) pp. 323-327.
Boeda, Fabien et al., Phosphabicyclononane-Containing Ru Complexes: Efficient Pre-Catalysts for Olefin Metathesis Reactions, J. Org. Chem. 2008, 73, pp. 259-263.
Schwab, Peter et al., Synthesis and Applications of RuCl2(=CHR')(PR3)2: The Influence of the Alkylidene Moiety on Metathesis Activity, J. Am. Chem. Soc. 1996, 118, pp. 100-110.
Carreira, Monica et al., Anatomy of Phobanes, Diastereoselective Synthesis of the Three Isomers of n-Butylphobane and a Comparison of their Donor Properties, J. Am. Chem. Soc. 2009, 131, pp. 3078-3092.
Mele, Giuseppe et al., Synthesis of novel porphyrins cardanol based via cross metathesis; Catalysis Today 140 (2009) pp. 37-43.
Vasapollo, Giuseppe et al., Cardanol-Based Materials as Natural Precursors for Olefin Metathesis, Molecules 2011, 16, pp. 6871-6882.
British Search Report, Application No. GB1216463.8, The University Court of the University of St. Andrews, Jan. 10, 2013.
Guo, Ying-Cen et al., An efficient route to biscardanol derivatives and cardanol-based porphyrins via olefin metathesis, Journal of Organometallic Chemistry 691 (2006) pp. 5383-5390.
Mmongoyo, Juma A. et al., Synthesis of a kairomone and other chemicals from cardanol, a renewable resource, Eur. J. Lipid Sci. Technol. 2012, 114, pp. 1183-1192.
Forman, Grant S. et al., A Convenient System for Improving the Efficiency of First-Generation Ruthenium Olefin Metathesis Catalysts, Organometallics 2005, 25, pp. 4528-4542.
Vougioukalakis, Georgios C. et al., Ruthenium-Based Heterocyclic Carbene-Coordinated Olefin Metathesis Catalysts, Chem. Rev. 2010, 110, pp. 1746-1787.
Forman, Grant S. et al., Metathesis of renewable unsaturated fatty acid esters catalysed by a phoban-indenylidene ruthenium catalyst, Journal of Organometallic Chemistry 691 (2006), pp. 5513-5516.
Sanford, Melanie S., et al., Mechanism and Activity of Ruthenium Olefin Metathesis Catalysts, J. Am. Chem. Soc. 2001, 123, pp. 6543-6554.
Webb, Paul B. et al., Continuous Flow Hydroformylation of Alkenes in Supercritical Fluid-Ionic Liquid Biphasic Systems, J. Am. Chem. Soc. 2003, 125, pp. 15577-15588.
Duque, Ruben et al., Continuous flow homogeneous alkene metathesis with built-in catalyst separation, Green Chem., 2011, 13, pp. 1187-1195.
Grubbs, Robert H., Olefin-Metathesis Catalysts for the Preparation of Molecules and Materials (Nobel Lecture), Angew. Chem. Int. Ed 2006, 45, pp. 3760-3765.

(Continued)

*Primary Examiner* — Rosalynd Keys
(74) *Attorney, Agent, or Firm* — McDonald Hopkins LLC

(57) ABSTRACT

The invention provides a method of alkene metathesis comprising contacting at least a first alkene, which is cardanol and/or anacardic acid, with an alkylidene ruthenium alkene metathesis catalyst comprising two ligands $P^1$ and $P^2$, which may be the same or different and of formula $P(R^1)_3$, in which P is a phosphorus atom coordinated to the ruthenium ion and each $R^1$ is independently an optionally substituted alkyl or alkoxy group; or two $R^1$ groups within one $P^1$ or $P^2$ ligand constitute an optionally substituted bicycloalkyl.

14 Claims, No Drawings

(56) References Cited

OTHER PUBLICATIONS

Grubbs, Robert H., Olefin metathesis, Tetrahedron 60 (2004), pp. 7117-7140.

Trnka, Tina M. et al., The Development of L2X2Ru=CHR Olefin Metathesis Catalysts: An Organometallic Success Story, Acc. Chem. Res. 2001, 34, pp. 18-29.

International Search Report and the Written Opinion of the International Searching Authority, PCT/GB2013/052371, University Court of the Universith of St Andrews., Nov. 29, 2013.

Hintermair, Ulrich et al., Continuous flow hydroformylation using supported ionic liquid phase catalysts with carbon dioxide as a carrier, Dalton Trans., 2010, 39, pp. 8501-8510.

\* cited by examiner

METATHESIS REACTIONS WITH CARDANOL AND/OR ANACARDIC ACID

RELATED APPLICATION DATA

This patent application is a national phase application of and claims priority to PCT/GB2013/052371, filed Sep. 11, 2013, which itself claims priority to GB Application No. 1216463.8, filed Sep. 14, 2012, and GB Application No. 1216491.9, filed Sep. 14, 2012.

FIELD

The invention relates to a method of metathesis of one or more unsaturated compounds, generally one or more alkenes. In the method, at least one unsaturated compound comprises a non-aromatic carbon-carbon double bond tethered to an aromatic alcohol, such as a phenol, is contacted with a metathesis catalyst.

BACKGROUND

Olefin (alkene) metathesis is a very well-known synthetic technique, which allows the exchange of substituents between alkenes by transalkylidenation. In recent years, metathesis reactions have been the study of intense research Indeed, the 2005 Nobel Prize in Chemistry was awarded jointly to the chemists Yves Chauvin, Robert H. Grubbs and Richard R. Schrock *"for the development of the metathesis method in organic synthesis"*.

Such redistribution of carbon-carbon double bonds is catalysed by transition metal-containing catalysts. The most common transition metal used is ruthenium, in the form of alkylidene-containing complexes (so-called alkylidene ruthenium complexes, or catalysts), more typically still alkylidene ruthenium complexes which comprise two (generally) neutral ligands and two additional anionic ligands. For a comprehensive review of such alkylidene ruthenium metathesis catalysts, the reader is referred to Ruthenium-based Heterocyclic Carbene-Coordinated Olefin Metathesis Catalysts (G C Vougioukalakis and R H Grubbs, *Chem. Rev.*, 2010, 110, 1746-1787). In this review, emphasis is, as it typically is in the art, focused on the use of catalysts comprising carbene-containing, in particular, N-heterocyclic carbene-containing (NHC-containing) catalysts, the improved thermal and oxidative stability of such catalysts being believed to be attributable to the decreased lability of such carbenes as compared with phosphine ligands, for example, as well as other ligands coordinating through phosphorus atoms, such as phosphites, phosphinites or phosphonites. Indeed, there has been a discernible move away from metathesis catalysts comprising only phosphines as the neutral ligands in favour of carbenes, in particular N-heterocyclic carbenes.

The earliest well-defined alkylidene- and ruthenium-containing metathesis catalysts comprised two phosphine ligands and are often referred to as "First Generation" catalysts. The archetypal First Generation Grubbs catalyst is 1. Developments in this technology led to 2, the first of the so-called "Second Generation" metathesis catalysts, in which one of the tri(cyclohexyl) phosphine ligands (P(Cy)$_3$ ligands) of 1 has been replaced with an NHC. Sometimes, including herein, catalysts of the type epitomised by 1 and 2, i.e. alkylidene ruthenium catalysts with two discrete neutral ligands are referred to as Grubbs metathesis catalysts, or simply Grubbs catalysts, Still further evolution afforded the so-called Hoveyda-Grubbs catalyst 3, which was reported in the year 2000. This phosphine-free catalyst comprises a coordinating isopropoxy substituent attached to the aromatic ring of the benzylidene group, which replaces one of the neutral ligands. This catalyst and variants of it have proven popular owing to their improved thermal stability and oxygen- and moisture-tolerance in comparison with 1 and 2.

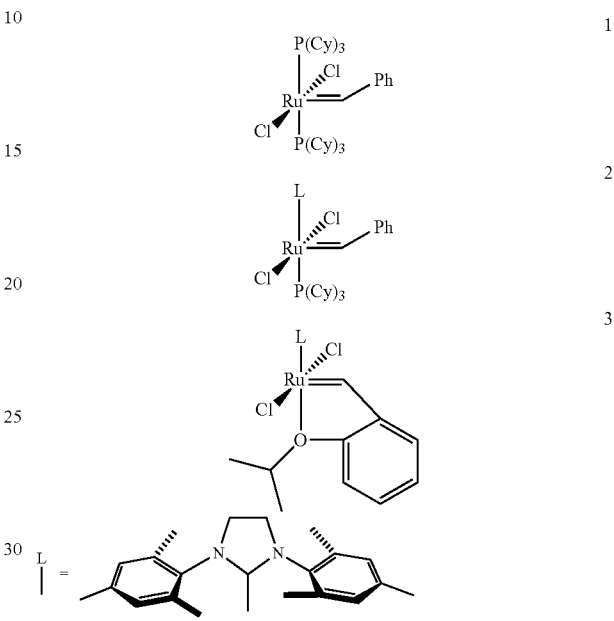

Olefin metathesis reactions may be divided into a variety of subclasses. These include, but are not limited to, so-called cross metathesis, ring-closing metathesis, ring-opening metathesis polymerisation (often referred to as ROMP) and self metathesis reactions.

Cross metathesis appears to be subject to a variety of definitions in the literature, including for example a metathesis reaction between two non-cyclic olefins, and an intermolecular metathesis reaction between terminal alkenes. However, cross metathesis as defined herein is any metathesis reaction between two alkenes. Typically the two alkenes participating in a cross metathesis will be acyclic. It will be understood that, where the participating alkenes are the same, such a cross metathesis reaction is an example of self metathesis. Typically, however, cross metatheses are not self metathetic.

Ring-closing metathesis is a reaction whereby a ring is formed as a result of a metathesis reaction between two carbon-carbon double bonds. For example, an acyclic diene, typically in which the two participating C=C bonds are terminal may be ring-closed. In contrast, ring-opening metathesis polymerisation involves, as the name implies, both ring-opening of a cycloalkene and polymerisation of the resultant diene.

Each of these (and other) classes of metathesis reactions are well-known to and understood by the skilled person and, as discussed above, may be and often are catalysed by alkylidene ruthenium complexes.

G S Forman et al. (Organometallics, 2005, 24, 4528-4542) report enhancement to the performance of certain olefin metathesis reactions catalysed by Grubbs catalysts by the simple addition of phenol or a substituted phenol. In a published patent application (WO 2004/056728 A1), similar metathesis reactions are described. In neither of these publications, however, is it in any way described or contemplated that the substituted phenol may be tethered to a C=C bond participating in a metathesis reaction, in other words that a phenol-comprising molecule participates in a metathesis reaction.

J A Mmongoyo et al. (*Eur. J. Lipid Sci. Technol.*, doi: 10.1002/ejlt.201200097) describe a specific example of a cross metathesis reaction between ethylene and cardanol. Cardanol is a term used to refer to a mixture of compounds each of which is a phenol having a $C_{15}$ hydrocarbyl straight chain at the 3-position and which vary in the degree of internal unsaturation in the chain, which has between 0 and 3 carbon-carbon double bonds. The type of scissile cross metathesis reaction described in this publication is sometimes referred to as ethenolysis, since the metathesis reaction between ethylene and an internal double bond serves to cleave the internal C=C bond. The ethenolysis described is catalysed by the Hoveyda-Grubbs catalyst (3, infra) is described as providing a less than perfect yield, with the reaction giving undesired quantities of other products believed to result from a series of side or competing reactions.

There is a continual need for modifications and/or improvements to existing metathesis methodologies and the present invention addresses this need in the art.

SUMMARY

The present invention is based, in part, upon the surprising finding of the advantageousness of conducting metathesis reactions, in which a participating C=C bond is tethered to an aromatic alcohol, in the presence of a specific subclass of Grubbs catalyst, namely those comprising two phosphine, phosphite, phosphinite or phosphonate ligands. This is surprising given the overwhelming prevalence for the use of "phosphorus-free" and/or carbene-based (in particular NHC-based) catalysts for metathesis, including those which comprise a chelating alkoxybenzylidene ligand, such as the Grubbs-Hoveyda catalyst. Indeed, the decreased lability of carbene-based ligands is suspected to give rise to the generally superior stability (both oxidative and thermal) of complexes containing these ligands, in comparison with phosphorus-coordinating analogues such as phosphines. This makes the present invention all the more unexpected.

Viewed from one aspect, therefore, the invention provides a method of alkene metathesis comprising contacting at least a first alkene, which comprises a carbon-carbon double bond tethered to an aromatic alcohol, in the presence of a alkylidene ruthenium alkene metathesis catalyst comprising two ligands $P^1$ and $P^2$, which may be the same or different and of formula $P(R^1)_3$, in which P is a phosphorus atom coordinated to the ruthenium ion and each $R^1$ is independently an optionally substituted alkyl or alkoxy group; or two $R^1$ groups within one $P^1$ or $P^2$ ligand constitute an optionally substituted bicycloalkyl.

In a particular variant of the first aspect of the invention, $P^1$ and $P^2$ are each independently of formula $P(R^1)_3$, in which P is a phosphorus atom coordinating to the ruthenium ion and each $R^1$ is independently an optionally substituted alkyl, alkoxy, aryl or aryloxy group; or two $R^1$ groups within one $P^1$ or $P^2$ ligand of formula $P(R^1)_3$ constitutes an optionally substituted bicycloalkyl.

Viewed from a second aspect, the invention provides an alkene obtained, or obtainable, by the method of the first aspect of the invention, or the variant thereof described immediately hereinbefore.

Further aspects and embodiments of the present invention will become apparent from the detailed discussion of the invention that follows below.

DETAILED DESCRIPTION

According to the method of the invention, particular alkylidene ruthenium catalysts are used to catalyse alkene metathesis reactions. The expression "used to catalyse" herein indicates that that the catalyst may be used to promote a metathesis reaction, e.g. a cross metathesis reaction, in a substoichiometric amount (relative to the alkenic substrate(s) undergoing metathesis), i.e. less than 1 molar equivalent (100 mol %) relative to at least the first alkene.

The expression "used to catalyse" does not require that the alkylidene ruthenium catalysts with which the alkene(s) is or are contacted are the actual catalytic species since, without wishing to be bound by theory, the alkylidene group in such catalysts is believed to be lost in the first catalytic cycle and the actual catalytic species may be formed in situ by alkylidene exchange with a double bond. Typical substoichiometric amounts will be in the range of about 0.0000001 to about 0.2 molar equivalents, e.g. about 0.00001 to about 0.2 molar equivalents, typically about 0.0001 to about 0.02 molar equivalents, relative to the amount of the first alkene. (Where a second alkene is employed in the metathesis reaction, its stoichiometry can be adjudged as appropriate by the skilled person).

Generally, the alkylidene ruthenium catalysts will be of formula (I):

(I)

wherein:
$P^1$ and $P^2$ are as herein defined;
$X^1$ and $X^2$ are anionic ligands, which may be the same or different; the and
A is an alkylidene group.

Typically the alkylidene ruthenium catalysts used comprise ruthenium ions, generally in oxidation state +2. It will be understood that these are may be formed in situ or ex situ.

Unless the context specifically suggests otherwise, the term "halide" refers to fluoride, chloride, bromide or iodide, typically chloride, bromide or iodide.

The term aromatic used herein embraces within its scope heteroaromatic. As known to those skilled in the art, heteroaromatic moieties are a subset of aromatic moieties that comprise one or more heteroatoms, typically O, N or S, in place of one or more ring carbon atoms and any hydrogen atoms attached thereto. Such exemplary heteroaromatic moieties, for example, include pyridine, furan, pyrrole and pyrimidine.

Aromatic moieties may be polycyclic, i.e. comprising two or more fused aromatic (including heteroaromatic) rings. Naphthalene and anthracene are examples of polycyclic aromatic moieties, and benzimidazole is an example of a polycyclic heteroaromatic moiety.

Unless the context herein specifically suggests otherwise, aromatic moieties, including aryl and arylene radicals and diradicals (formed formally by abstraction of one or two hydrogen atoms from an aromatic moiety) may be optionally substituted with one or more substituents selected from halo (e.g. fluoro, chloro, bromo and iodo), alkyl, aryl (including heteroaryl), hydroxy, nitro, amino, alkoxy, alkylthio, carboxy, cyano, thio, formyl, ester, acyl, thioacyl, amido, carbamido and sulfonamide.

Unless the context herein specifically suggests otherwise, by alkyl is meant herein a saturated hydrocarbyl moiety, which may be straight-chain, cyclic or branched. By alkylene is meant an alkyl group from which a hydrogen atom has been formally abstracted. Typically alkyl and alkylene groups will comprise from 1 to 25 carbon atoms, more usually 1 to 10 carbon atoms, more usually still 1 to 6 carbon atoms. Alkyl and alkylene groups may be substituted, for example once, twice, or three times, e.g. once, i.e. formally replacing one or more hydrogen atoms of the group. Examples of such substituents are halo (e.g. fluoro, chloro, bromo and iodo), aryl, heteroaryl, hydroxy, nitro, amino, alkoxy, alkylthio, carboxylate, sulfonate, phosphate, cyano, thio, formyl, ester, acyl, thioacyl, amido, carbamido, sulfonamido and the like. Examples of aryl (e.g. heteroaryl) substituted alkyl (i.e. aralkyl (e.g. heteroaralkyl)) include $CH_2$-aryl (e.g. benzyl) and $CH_2$-heteroaryl.

By alkene is meant a compound comprising one or more non-aromatic carbon-carbon double bonds.

By alkyne is meant a compound comprising one or more carbon-carbon triple bonds.

By carboxy is meant herein the functional group $CO_2H$, which may be in deprotonated form ($CO_2^-$).

By acyl and thioacyl are meant the functional groups of formulae —C(O)-alkyl or —C(S)-alkyl respectively, where alkyl is as defined hereinbefore.

By amido is meant a functional group comprising the moiety —N(H)C(=O)—;

By carbamido is meant a functional group comprising the moiety —N(H)C(=O)N(H)—;

By ester is meant a functional group comprising the moiety —OC(=O)—;

By sulfonamido is meant a functional group comprising the moiety —$SO_2NH$— in which the hydrogen atom depicted may be replaced with alkyl or aryl.

Alkyloxy (synonymous with alkoxy) and alkylthio moieties are of the formulae —O-alkyl and —S-alkyl respectively, where alkyl is as defined hereinbefore.

Aryloxy and arylthio moieties are of the formulae —O-aryl and —S-aryl respectively, where aryl is as defined hereinbefore.

Alkylamino and dialkylamino moieties are of the formulae —N(H)-alkyl and alkyl

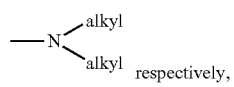

respectively, where alkyl is as defined hereinbefore.

By amino group is meant herein a group of the formula —$N(R^x)_2$ in which each $R^x$ is independently hydrogen, alkyl or aryl, e.g. an unsaturated, unsubstituted $C_{1-6}$ hydrocarbyl, e.g. alkyl such as methyl or ethyl, or in which the two $R^x$s attached to the nitrogen atom N are connected. One example of this is whereby —$R^x$—$R^x$— forms an alkylene diradical, derived formally from an alkane from which two hydrogen atoms have been abstracted, typically from terminal carbon atoms, whereby to form a ring together with the nitrogen atom of the amine. As is known the diradical in cyclic amines need not necessarily be purely hydrocarbyl (the alkylene chain —$R^x$—$R^x$— may be interrupted by, for example, one or more heteroatoms (e.g. O, S or NR, wherein R is hydrogen, alkyl or aryl), or indeed saturated: morpholine (in which —$R^x$—$R^x$— is —$(CH_2)_2O(CH_2)_2$—) is one such example of a cyclic amino in which an alkylene chain is interrupted by oxygen.

References to amino herein are also to be understood as embracing within their ambit quaternised or protonated derivatives of the amines resultant from compounds comprising such amino groups. Examples of the latter may be understood to be salts such as hydrochloride salts.

The alkylidene ruthenium catalysts of the present invention typically comprise two anionic ligands ($X^1$ and $X^2$ in formula (I)). These anionic ligands are not particularly limited. Examples include those described in section 7 of G C Vougioukalakis and R H Grubbs (infra). For example, in addition to the often-used halides, anionic ligands may be alkyl or aryl carboxylates or sulfonates, alkoxides or aryloxides optionally in which one or more hydrogen atoms within the alkyl or aryl moieties of such ligands have been substituted with halogen atoms, notably fluorine, for example in which the alkyl or aryl moieties of such ligands have been perfluorinated (by which is meant that all of the hydrogen atoms of hydrocarbyl group R replaced with fluorine). Specific examples of such anionic ligands include acetate, monofluoroacetate, difluoroacetate, trifluoroacetate, propionate, perfluoropropionate, $C_{1-6}$alkoxides such as methoxide, ethoxide and tert-butoxide, phenoxide, perfluorophenoxide, tosylate, mesylate and triflate. In many embodiments, $X^1$ and $X^2$ will be the same. In many embodiments, $X^1$ and $X^2$ will be halide, typically but not necessarily chloride; bromide and iodide may also be used. In particular embodiments $X^1$ and $X^2$ are each chloride.

Ligands $P^1$ and $P^2$ are each independently of formula $P(R^1)_3$. Whilst these ligands may be the same or different, typically they are the same.

Either or both of $P^1$ and $P^2$ may be a phosphine, phosphite, phosphinite or phosphonite. In accordance with the skilled person's understanding of these four classes of phosphorus-containing compound: the terms of their normal meanings: phosphine used herein defines a compound of formula $P(R^1)^3$, in which each $R^1$ is independently optionally substituted alkyl; or two $R^1$ groups within one $P^1$ or $P^2$ ligand of formula $P(R^1)^3$ constitutes an optionally substituted bicycloalkyl; the term phosphite used herein defines a compound of formula $P(R^1)^3$, in which each $R^1$ is independently optionally substituted alkoxy; the term phosphonite used herein defines a compound of formula $P(R^1)^3$, in which one $R^1$ group is optionally substituted alkyl and two $R^1$ groups are independently optionally substituted alkoxy; and the term phosphinite defines a compound of formula $P(R^1)^3$, in which two $R^1$ groups are independently optionally substituted alkyl or together constitute an optionally substituted bicycloalkyl and one $R^1$ is independently optionally substituted alkoxy.

Typically, although not necessarily, each $P^1$ and $P^2$ is a phosphine or phosphite, for example each $P^1$ and $P^2$ is a phosphine. In each of these embodiments, (i.e. wherein $P^1$ and $P^2$ is a phosphine, phosphite, phosphinite or phosphonite; phosphine or phosphite; or a phosphine), $P^1$ is typically the same as $P^2$.

Typically, although not necessarily, each of the discrete $R^1$ groups within the $P^1$ and $P^2$ ligands comprise from 1 to 20 carbon atoms. The term "discrete $R^1$ groups" is intended to exclude the possibility for two $R^1$ groups together constituting an optionally substituted bicycloalkyl, which optionally substituted bicycloalkyl typically comprises from 8 to 12 carbon atoms. More commonly, at least two of the discrete $R^1$ groups comprise between 5 and 10 carbon atoms, for example all of the discrete $R^1$ groups comprise between 5 and 10 carbon atoms.

The skilled person is very familiar with $P^1$ and $P^2$ ligands suitable for use in alkylidene ruthenium metathesis catalysts. In particular, it is often advantageous for at least two $R^1$ groups to be or comprise a branched alkyl or cycloalkyl group. According to particular embodiments of the invention, $P^1$ and $P^2$ are tricycloalkylphosphines and tricycloalkylphosphites, in particular tricyclopentylphosphine, tricyclopentylphosphite, tricyclohexylphosphine and tricyclohexyphosphite. According to many embodiments of the invention, at least one $P(R^1)_3$ group, and typically both $P(R^1)_3$ groups are, tricyclohexylphosphine. Notwithstanding this, however, the skilled person is well aware of the suitability of many other phosphorus-coordinating ligands suitable for use with alkylidene ruthenium metathesis catalysts. For example, reference may be made to tri(tert-butyl)phosphine and tri(iso-propyl)phosphine.

Whilst attention is focused in the present discussion on the use of alkyl-based $P^1$ and $P^2$ groups, the invention is not to be understand to be so limited, the discussion here of such embodiments of the invention also applying mutatis mutandis to the variant of the first aspect of the invention described above in which one or more $R^1$ groups may be aryl or aryloxy.

With regard to the possibility of two $R^1$ groups within one ligand of formula $P(R^1)_3$ group constituting a bicycloalkyl group, the skilled person will be aware of the description in the art of the use of so-called phobanes—9-phosphabicyclononanes—in metathesis catalysis. In this regard, reference is made to F Boeda et al. (*J. Org. Chem.,* 2008, 73(1), 259-263), M Carreira et al. (*J. Am. Chem. Soc.,* 2009, 131(8), 3078-3092), G S Forman et al. (*J. Organomet. Chem.,* 2006, 691, 5513-5516) and WO 2007/010453 A2 (Sasol Technology (UK) Limited) and the technology described therein. According to particular embodiments of the invention one or both $P(R^1)_3$ groups may be a phobane. In these and other $P^1$ and $P^2$ ligands, the phosphorus atoms are in particular embodiments additionally attached to an alkyl, e.g. cycloalkyl group, for example one comprising between 4 and 20 carbon atoms (e.g. tert-butyl, sec-butyl, cyclohexyl or eicosyl). Phobane-containing metathesis catalysts are available commercially, e.g. from Cytec or Umicore.

In many embodiments of the invention, the $R^1$ groups within $P^1$ and $P^2$ are unsubstituted. Where an $R^1$ group is substituted, however (including embodiments in which two $R^1$ groups within one ligand of formula $P(R^1)_3$ is a substituted bicycloalkyl group), such $R^1$ groups may comprise one or more substituents with which alkyl groups may generally be substituted (vide infra). Notwithstanding this, a $R^1$ group may according to particular embodiments comprise one or more halo substituents; a sulfonate ($—SO_3^-$), phosphate ($—OPO_3^{2-}$) or carboxylate ($—CO_2^-$) group; a quaternary ammonium group; or a poly(ethylene glycol)-containing (PEG-containing) substituent.

Where the substituent of a $R^1$ group is halo, this may be, although not necessarily is, fluoro. Moreover, in particular embodiments, multiple fluoro substitution may be effected, so as to provide perfluorinated $R^1$ groups, or $R^1$ groups comprising perfluorinated portions. As an example of the latter, reference is made to compound 421 in Vougioukalakis and R H Grubbs (infra), and the references cited therein. Compound 421 comprises a partially perfluorinated trialkyl phosphine in which each of the groups of the phosphine is a perfluorodecylethyl moiety. As is described, such fluorine substitution can be advantageous in effecting metathesis reactions in both monophasic and biphasic solvent mixtures (for example in dichloromethane and dichloromethane/fluorine-containing solvent mixtures) with improved reaction rates found when conducting metathesis reactions in such biphasic solvent mixtures.

Where a substituent of an $R^1$ group is a quaternary ammonium group, this may typically be a group of the formula $—N+(R^2)^3(X^3)—$, wherein each $R^2$ is alkyl or aryl, typically alkyl; and $X^3$ is any convenient anion. However, such $R^1$ substitution is not so limited and the skilled person will be aware of the possibility of substituting $R^1$ with more structurally complicated quaternary ammonium moieties such as alkylene- or alkyleneoxy-linked imidazolium and pyrrolidinium cations.

Where a substituent of an $R^1$ group is a PEG-containing substituent, wherein PEG comprises a plurality, e.g. 2 to 2000, consecutive units of $—CH_2CH_2O—$, typically only one of $P^1$ and $P^2$ will be substituted in this way.

Catalysts comprising sulfonate ($—SO_3^-$), phosphate ($—OPO_3^{2-}$), carboxylate ($—CO_2^-$) or quaternary ammonium groups or PEG-containing substituents, can be advantageous, as is known in the art, in permitting metathesis to be effected in water and/or protic solvents such as alcohols (for example $C_{1-6}$ alcohols such as methanol or ethanol), or combinations of such solvents or mixtures of other solvents with other solvents with which these solvents or mixtures of solvents are miscible, for example dimethylformamide (DMF) and dimethyl sulfoxide (DMSO). Catalysts comprising sulfonate ($—SO_3—$), phosphate ($—OPO_{32}$), carboxylate ($—CO_2—$) or quaternary ammonium groups also may be used to effect metathesis catalysis in ionic liquids, as described in more detail below. Introduction of each of these substituents into $R^1$ groups is within the capability of those skilled in the art and, in this regard, reference is made to the technology described in section 9 of the article by G C Vougioukalakis and R H Grubbs (infra), and the references cited therein. The skilled person will understand that the teaching in this reference (in relation to substitution of NHC-containing catalysts, both on the NHC ligands themselves as well as other parts of alkylidene ruthenium metathesis catalysts, may be applied mutatis mutandis to phosphorus-containing ligands in accordance with the present invention. For example, WO 01/46096 (Sasol Technology (Pty) Ltd) describes a alkylidene ruthenium metathesis catalyst comprising two dicyclohexyl ((trimethylammonium) ethyl)phosphine ligands having solubility in both water and methanol.

Where the substituent of a $R^1$ group is a quaternary ammonium group, the nature of the counteranion (to the quaternary ammonium group) is not of particular consequence. Any convenient an ion may be used. Halide anions such as chloride anions are typical although the skilled person will be able to identify other suitable anions without difficulty.

Whilst substitution with a sulfonate, phosphate or carboxylate group is advantageous in the context of conducting metathesis reactions in solutions comprising water and/or protic solvents, as discussed infra, in which the identity of the countercation to these groups is not of particular importance, and may for example be an alkali or alkaline earth cation (such as $Na^+$, $Li^+$, $K^+$ or $Ca^{2+}$, for example), the introduction of such substituents also offers the possibility of conducting metathesis reactions in ionic liquids, in particular with the group is sulfonate.

The alkylidene group (=A in formula (I)) may be any suitable alkylidene group for use in ruthenium-catalysed metathesis. The skilled person is aware of a wealth of information regarding the various possibilities for the alkylidene group, as well as methods of making such alkylidene-containing catalysts. In this regard, reference is made yet again to G C Vougioukalakis and R H Grubbs (infra), as well as P Schwab et al. (*J. Am. Chem. Soc.* 1996, 118, 100-110) and P Schwab et al. (*Angew. Chem., Int. Ed. Engl.,* 1995, 34, 2039-2041) and the description throughout as to the various possibilities for the alkylidene group in catalysts of this type, including the variants expressly described in section 5 of Vougioukalakis and Grubbs. Typically, the alkylidene group may be defined as a moiety of formula $=CR^yR^z$, wherein "=C" indicates the bonding with the ruthenium ion. One of $R^y$ and $R^z$ may be hydrogen and either or both of $R^y$ and $R^z$ may be alkyl, alkenyl, alkynyl, aryl carboxyalkyl, alkoxy, alkenyloxy, alkynyloxy or alkoxycarbonyl, or $R^y$ and $R^z$ together form a saturated, unsaturated or aromatic cyclic or bicyclic moiety. Those of skill in the art will recognise that where $R^y$ and $R^z$ together form a bicyclic moiety, this embraces the indenylidene alkylidenes first reported by Nolan et al. in 1999, and which are often employed in contemporary metathesis catalysis, in particular the 3-phenyl-1H-inden-1-ylidenes. According to particular embodiments, the alkylidene group may be indenylidene, for example an aryl-, e.g. phenyl-, substituted indenylidene, e.g. 3-phenyl-1H-inden-1-ylidene. However, the invention should in no way be considered to be so-limited. For example, the alkylidene group may embrace moieties of formula $=CR^yR^z$, wherein $R^y$ is hydrogen, alkyl or aryl and $R^z$ is alkyl, alkenyl or aryl, more particularly wherein $R^z$ is phenyl or vinyl, either an unsubstituted or substituted with halo, nitro, amino (e.g. dimethylamino), alkyl (e.g. methyl), alkoxy (e.g. methoxy) and aryl (e.g. phenyl).

The alkylidene ruthenium catalysts used may be formed in situ or ex situ. Catalysts prepared ex situ are often referred to in the art as being well-defined. "Well-defined" means, as is understood by those skilled in the art, and is meant herein, a complex that is prepared ex situ, and is thus susceptible to characterisation (i.e. definition). In other words, the use of a well-defined complex means that the environment, for example, a reaction vessel, in which the substrate(s) for the metathesis reaction are contacted with the catalyst of formula (I) is charged a pre-formed transition metal catalyst of formula (I), rather than precursors to such transition metal complexes formed in situ.

Alternatively, as is known, the catalyst of formula (I) may be formed in situ. Reference is made in this regard, for example, to P O Nubel and C L Hunt (*J. Molec. Catal. A: Chemical,* 1999, 145(1-2), 323-327) and U.S. Pat. No. 6,159,890 which describe catalyst systems from which catalytically active species may be generated in situ. As is described in these publications, a source for the ruthenium ion in the metathesis catalyst, as well as a source of the desired neutral ligands (which according to the present invention are of the phosphorus-coordinating ligands $P^1$ and $P^2$), anionic ligands and for the alkylidene group are brought into contact. In such in situ embodiments, the method of the invention will thus typically involve bringing together these components in an environment, for example, a reaction vessel, in which the substrate(s) for the metathesis reaction are to be contacted, together with the substrate(s) for the desired alkene metathesis, i.e. at least a first alkene.

The source of the ruthenium ion is typically an inorganic salt such as ruthenium halide, e.g. chloride, for example ruthenium (III) chloride, optionally as a hydrate thereof. Advantageously, such salts also provide anionic ligands $X^1$ and $X^2$, i.e. where these ligands are the halide ions of the ruthenium halide. Alternatively, they may be introduced separately.

The source of the alkylidene A may be an alcohol. For example, where the alkylidene is 3-phenyl-1H-iden-1-ylidene, this may be made by a reaction between a source for the ruthenium (II) ion within the catalyst of formula (I) and 1,1-diphenyl-2-propyn-1-ol. The skilled person is well aware of how to make ruthenium indenylidene complexes (see, for example, F Boeda et al. (*Chem. Commun.,* 2008, 2726-2740).

The source of the ruthenium ion is typically an inorganic salt such as ruthenium halide, e.g. chloride, for example ruthenium (III) chloride, optionally as a hydrate thereof. Advantageously, such salts also provide anionic ligands $X^1$ and $X^2$, i.e. where these ligands are the halide ions of the ruthenium halide. Alternatively, they may be introduced separately.

Whilst it is possible to make catalysts of formula (I) in situ, this is not at all essential, the synthesis of well-defined alkylidene ruthenium catalysts for use in the present invention, including those of formula (I), being at the disposal of the skilled person. Moreover, such catalysts are readily available commercially, for example from Umicore AG & Co. KG, Germany, and other suppliers of metathesis catalysts with which the skilled person is very familiar. Specific examples of catalysts include the First Generation catalysts dichloro(3-phenyl-1H-inden-1-ylidene)bis(tricyclohexylphosphine) ruthenium (II) and (3-phenyl-1H-iden-1-ylidene)bis(isobutylphobane) ruthenium (II), sold as M1 and $M1_1$ respectively by Umicore.

Mention is now made of the nature of the substrate(s) for the metathesis reaction. A characteristic feature of the present invention is that at least one alkene, herein the "first alkene", participating in the metathesis reaction of the invention comprises an aromatic alcohol, to which the carbon-carbon double bond characterising the first alkene is tethered.

By "aromatic alcohol" is meant herein a compound of formula $R^3OH$ in which $R^3$ to which the hydroxy group is attached is an aromatic ring. As stated above, the term aromatic embraces within its scope heteroaromatic. The complement to heteroaromatic, whereby to refer to aromatic compounds not comprising any heteroatoms in the aromatic ring, is to refer to aromatic hydrocarbons. It should be noted that use of this term does not exclude the possibility that such aromatic compounds are substituted with heteroatom-containing substituents. Typically, $R^3$ is an optionally substituted aromatic hydrocarbon, by which is meant that the aromatic hydrocarbon may comprise one or more additional substituents over and above the alkene-containing moiety and the hydroxyl group.

The aromatic ring to which the hydroxyl group of the aromatic alcohol is attached may be a monocycle, i.e. in which the aromatic ring to which the hydroxyl group is fused is not fused to any other rings. Alternatively, this aromatic ring may be part of a polycyclic system, i.e. in which it is fused to one or more aromatic (including heteroaromatic) or non-aromatic rings. Napthalene, anthracene and phenanthrene are examples of fully aromatic polycyclic hydrocarbons (a bicycle and two tricycles respectively), and benzimidazole is an example of a fully aromatic polycyclic heteroaromatic compound. 1,2,3,4-tetrahydronaphthalene is an example of a compound comprising an aromatic ring fused to a non-aromatic ring.

Typically, when the hydroxyl-bearing aromatic ring is part of a polycyclic system, this will be a fully aromatic system. Examples of such aromatic alcohols include, for example, napthol (1- or 2-) and phenanthrol (e.g. 9-phenanthrol).

Whilst the hydroxy-substituted aromatic ring of the aromatic alcohol may be part of a polycyclic system, in many embodiments the aromatic alcohol is monocyclic, that is to say the hydroxy-substituted aromatic ring is not fused to another ring. Within these embodiments of the invention, the hydroxy-substituted aromatic ring may be a phenol.

The aromatic alcohol may be subject to additional substitution (i.e. over and above the C=C— containing substituent. Such substituents may for example, be those mentioned above with which aromatic moieties may be substituted, for example halo, alkyl, aryl, hydroxy, nitro, amino, alkoxy, carboxyl, cyano, formyl, ester, acyl, amido, carbamido and sulfonamide. For example, the aromatic alcohol may be an aromatic diol or a hydroxybenzoic acid.

The first alkene comprises a carbene-carbon double bond tethered to the aromatic alcohol just described. By "tethered" is meant that the carbon-carbon double bond is connected to a ring atom of the aromatic alcohol, either to the same ring to which the hydroxyl group of the aromatic alcohol is attached, or to a ring fused thereto. The carbon-carbon double bond may in some embodiments be directly attached to the ring atom of the aromatic alcohol. Typically, however, it is connected to ring atom of the aromatic alcohol by a hydrocarbylene chain, optionally interrupted with ether, ester, amide or amine groups, wherein between 1 and about 25, more typically between about 1 and 10 atoms, separate the carbon-carbon double bond from the aromatic ring. The optionally interrupted hydrocarbylene chain may be optionally substituted. In many embodiments, however, it is unsubstituted. In many of these embodiments, it is also not interrupted, i.e. is a hydrocarbylene chain. In particular embodiments, such an uninterrupted, unsubstituted hydrocarbylene chain is an alkylene chain comprising between 1 and about 25, more typically between about 1 and 10, carbon atoms between the carbon-carbon double bond and the ring atom of the aromatic alcohol to which the hydrocarbylene chain is attached.

It is to be understood that the carbon-carbon double bond of the first alkene may be a terminal or internal double bond. Where the carbon-carbon bond of the first alkene is terminal, this means that one of its carbon atoms is tethered to the aromatic alcohol and the other is not substituted by any carbon atoms. Typically, however, the carbon-carbon bond of the first alkene is internal, by which is meant that one of its carbon atoms is connected to the aromatic alcohol by the hydrocarbylene chain, if present, and the other is connected to a hydrocarbyl group, the carbon atoms of which are optionally interrupted with ether, ester, amide or amine groups, comprising between 1 and about 25, more typically between about 1 and 10 atoms, from the first atom of the hydrocarbyl group attached to the carbon-carbon bond and its terminal carbon atom. This optionally interrupted hydrocarbyl group may be optionally substituted. In many embodiments, however, it is unsubstituted. In many of these embodiments, it is also not interrupted, i.e. is a hydrocarbyl group. In particular embodiments, such an uninterrupted, unsubstituted hydrocarbyl group comprises between 1 and about 25, more typically between about 1 and 10, carbon atoms.

It is further to be understood that the hydrocarbyl group may comprise further sites of unsaturation, including carbon-carbon double bonds. In this way, the first alkene participating in the metathesis reaction may, for example, comprise more than one carbon-carbon double bond, for example it may comprise two or three carbon-carbon double bonds. It will also be understood that, in order to be a substrate for the ring-closing metathesis, for example, the first alkene should comprise at least two carbon-carbon double bonds positioned within the molecule in such a way so as to allow the desired ring closure to be effected by way of the metathesis reaction. The skilled person is able to design compounds so as to devise structures suitable for effecting ring-closing (and ring-opening) metathesis reactions.

According to particular embodiments of the invention, the metathesis reaction is a cross metathesis reaction between the first alkene and a second alkene. There is no particular limitation on the nature of the second alkene. It may, for example, be any alkene, diene or polyene (the lattermost term referring to an unsaturated compound comprising three or more carbon-carbon double bonds, for example between 3 and 100 carbon-carbon double bonds). However, according to particular embodiments of the invention, the metathesis reaction is a cross metathesis reaction between the first alkene, which is an internal alkene, and a second monounsaturated alkene (i.e. a compound comprising one carbon-carbon double bond). According to specific embodiments, the second alkene is ethylene (ethene; $H_2C=CH_2$) and the first alkene comprises an internal carbon-carbon double bond. Cross metathesis between ethylene and such an internal carbon-carbon double bond effects ethenolysis of the carbon-carbon double bond within the first alkene and in particular embodiments of the invention such an ethenolysis reaction is particularly advantageous. According to other specific embodiments, the second alkene is but-2-ene.

The invention is now described with regard to a specific embodiment, the ethenolysis of phenolic compounds, including cardanol, found in cashew nut shell liquid (CNSL), the byproduct of the cashew nut processing industry, which is available in an amount of approximately 300,000-600,000 tonnes per year worldwide and which has so few uses that it is generally considered to be a waste stream.

CNSL predominantly comprises four phenolic compounds, the proportions of which vary naturally and also depend on the method by which CNSL is extracted from the shells of the cashew nuts. Typical compositions of CNSL (with the figures being molar percentages) obtained by solvent extraction or by roasting are indicated in Table 1 below:

TABLE 1

Typical composition of CNSL obtained by solvent extraction or by roasting. R is a $C_{15}$ hydrocarbyl chain with 1 to 3 double bonds, "*" indicating the end of the bond through which the hydrocarbyl chains —R below are attached to the aromatic ring:

| Component:- | Anacardic acid | Cardanol | Cardol | 2-Methylcardol |
|---|---|---|---|---|
| Solvent extraction | 65 | 10 | 15 | Trace |
| Roasting | 10 | 85 | 3 | 2 |

As is discussed by J A Mmongoyo et al. (infra), cardanol is generally used in the art, and is used in the same sense herein, to refer to a composition comprising a mixtures of compounds in which hydrocarbyl chain R varies in its degree of unsaturation, as indicated above. Similarly, the other components of CNSL, anacardic acid, cardol and 2-methylcardol are also used to refer to mixtures of compounds in which hydrocarbyl chain R varies in its degree of unsaturation The versatility of the components of CNSL, including but not limited to cardanol, as starting materials in synthesis arises from their structure and, amongst other reactions J A Mmongoyo et al. discuss, cross metathesis between ethylene and the unsaturated components within cardanol may be used to afford 1-octene and 3-non-8-enylphenol.

Accordingly, according to particular embodiments of the invention the method comprises contacting CNSL, or one or more components thereof, with the alkylidene ruthenium alkene metathesis catalyst. According to particular embodiments the method comprises contacting cardanol and/or anacardic acid, for example cardanol, with the alkylidene ruthenium alkene metathesis catalyst. In this way, the invention permits the preparation of 1-octene and 3-non-8-enylphenol. According to these embodiments, the metathesis reactions effected may be ethenolyses, i.e. cross metathesis reactions between one or more of the components of CNSL and ethylene. However, it will be understood by those skilled in the art that those components of CNSL comprising the trienic R group may self-metathesise, whereby to afford 3-non-8-enylphenol and cyclohexadiene. Such reactions are ring-closing self-metatheses.

According to a further particular embodiment of the invention, the method comprises the ethenolysis of a monoene component of cardanol, which may, for example, be prepared by selective transfer hydrogenation using $RuCl_3$, as described by J G de Vries et al. on 10 Jul. 2012 at the 18th International Symposium on Homogeneous Catalysis, Toulouse, France, 9-13 Jul. 2002. For example, the method may comprise the ethenolysis of

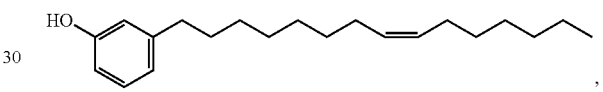

which may be prepared by the method described by J G de Vries et al.

According to particular embodiments, where a 3-non-8-enylphenol, for example 3-non-8-enylphenol, is prepared, this may be optionally subject to hydrogenation of the carbon-carbon double bond, whereby to provide a 3-nonylphenol, and further, ethoxylation of the phenol to provide an ethoxy-3-nonylphenol or oligoethoxy-3-nonylphenol, in which the phenol hydroxyl is replaced with —(OCH$_2$CH$_2$)$_n$OH, wherein n is an integer of between 1 and 20, typically between 3 and 15, e.g. 9. Suitable methods of hydrogenation and ethoxylation are well within the capability of those skilled in the art. The invention also extends to ethoxy-3-nonylphenol or oligoethoxy-3-nonylphenol obtainable or obtained by the method of the invention. Prior to hydrogenation, the 3-non-8-enylphenol may be subject to optional purification from other components (e.g. cyclohexadiene and/or 1-octene) resultant from the metathesis reaction by which it is prepared, according to the normal ability of those skilled in the art. Similarly, 1-octene may be readily subject to optional purification from other components (e.g. cyclohexadiene and/or 3-non-8-enylphenol) resultant from the metathesis reaction by which it is prepared.

General conditions for effecting metathesis reactions are well-known. Typically, the reactions will be conducted at temperatures ranging from about 10° C. to about 100° C., dependent on solvent and other factors, for between about 5 minutes and 24 hours. Dependent on the substrate(s) for the metathesis reactions, pressure may be used. For example, in ethenolyses, which are typically conducted in pressurised reactors, the pressure at which the reaction is conducted is generally in the range of about 1 bar (100 kPa) to about 100 bar (10,000 kPa).

As noted above, substitution of the $P^1$ and/or $P^2$ groups of the alkylidene ruthenium catalysts with a charged or PEG-containing moiety offers the opportunity to conduct the desired metathesis reactions in water and/or protic solvents. Whilst substitution with a sulfonate, phosphate, carboxylate or quaternary ammonium group is advantageous in the context of conducting metathesis reactions in solutions comprising such solvents, in which the identity of the countercation to the negatively charged groups is not of particular importance, and may for example be an alkali or alkaline earth cation (such as $Na^+$, $Li^+$, $K^+$ or $Ca^{2+}$, for example) and the identity of the counteranion to the quaternary ammonium group is also not of particular importance, and may for example be halide anion (such as $Cl^-$, for example), the introduction of such substituents also offers the possibility of conducting metathesis reactions in ionic liquids.

Ionic liquids have in recent years been found to be of utility in a wide variety of synthetic applications. These liquids can be advantageous for use as solvents or as other types of continuous liquid phase reaction media (as discussed further below) on account of their thermal stability, inflammability and lack of volatility. The nature of Ionic liquids is well known to those of skill in the art. Broadly speaking, an ionic liquid is salt, but one in which the ions are insufficiently well-coordinated for the compound to be other than a liquid below 150° C., more usually below 100° C., and in some embodiments even at room temperature—so-called room-temperature ionic liquids. In other words, ionic liquids are salts that form stable liquids at temperatures below 150° C. or lower. There are no particular limitations as to the specific types of ionic liquids that may be used as solvents for metathesis reactions in accordance with the present invention. One or more ionic liquids may be used. As will be readily understood, one of the specific advantages that use of ionic liquids confers is removal of the need to have a condenser in order to achieve a high-temperature liquid environment in which the method of the present invention may be conducted. Ionic liquids, with inherently low vapour pressure, allow the maintenance of constant temperature to be achieved over the course of the method of the invention, in contrast to the significant vapour pressures of the high-boiling point solvents typically used in the prior art. Such solvents inevitably cause a decrease in the temperature of a reaction vessel when the solvent condenses back in. Ionic liquids, therefore, permit not only an advantageously elevated temperature but allow a more homogeneous temperature to be maintained throughout the reaction. Typically, ionic liquids have either no, or negligible, vapour pressure.

Organic cations that may be present in ionic liquids may include, for example, quaternary ammonium, phosphonium, heteroaromatic, imidazolium and pyrrolidinium cations. The counteranions present in ionic liquids are likewise not particularly limited. For example, suitable anions include halide (e.g. chloride or bromide), nitrate, sulfate, hexafluorophosphate, tetrafluoroborate, bis(triflylmethylsulfonyl)imide, (the bis(triflylmethyl sulfonyl)imide anion being abbreviated here as $[NTf_2]$; it is also sometimes referred to as N[Tf]2 or [Tf]2N) anions. Others will be evident to those of skill in the art.

Ionic liquids that may be used include 1-alkyl-3-methylimidazolium bis(trifluoromethylsulfonyl)imide, 1-alkyl-3-methylimidazolium hexafluorophosphate, 1,1,3,3-tetralkylguanidinium lactate, alkylpyridinium tetrafluoroborate, 1-alkyl-3-alkylimidazolium tetrafluoroborate, 1-alkyl-3-alkylimidazolium bis(trifluoromethyl sulfonyl)imide 1-alkyl-3-alkyl-imidazolium tetrafluoroborate, trialkyl-n-tetradecylphosphonium bis(trifluoromethylsulfonyl)imide, 1-alkyl-1-alkyl-pyrrolidinium trifluoromethanesulfonate and thiol-functionalised ionic liquids, wherein each alkyl is independently $C_{1-20}$, for example $C_{2-20}$ or $C_{2-12}$. For example the ionic liquids may be 1-butyl-3-methylimidazolium bis(trifluoromethylsulfonyl)imide, 1-n-butyl-3-methylimidazolium hexafluorophosphate, 1,1,3,3-tetramethylguanidinium lactate, N-butylpyridinium tetrafluoroborate, 1-butyl-3-methylimidazolium tetrafluoroborate, 1-ethyl-3-methylimidazolium bis(trifluoromethyl sulfonyl)imide 1-ethyl-3-methyl-imidazolium tetrafluoroborate, tri-n-hexyl-n-tetradecylphosphonium bis(trifluoromethylsulfonyl)imide, 1-butyl-1-methyl-pyrrolidinium trifluoromethanesulfonate, all of the foregoing but in which the cation is instead 1-octyl-3-methylimidazolium; and thiol-functionalised ionic liquids. Ionic liquids are readily available commercially, e.g. from Cytec Industries, Inc. and by contractual arrangement with the Ionic Liquids Laboratory at the Queens University of Belfast (see quill.qub.ac.uk for further details).

Ionic liquids can be engineered to tune their advantageous properties such as stability, vapour low pressure and solvating ability so as to be safer and more environmentally friendly than conventional volatile, organic compounds. Consequentially, and because of the possibility of recycling, use of ionic liquids can simplify synthetic reactions when it is possible to substitute such ionic liquids for conventional solvents.

As is known by those skilled in the art, certain ionic liquids are, notwithstanding their advantages, susceptible to decomposition at elevated temperatures (for example in excess of 240° C.) in a normal oxygen-containing atmosphere. However, such decomposition may be mitigated where heating is conducted in an inert atmosphere. Suitable inert atmospheres (e.g. those from which oxygen and/or moisture is substantially excluded) may be achieved by means well known to those of skill in the art and may be provided through the use of purging using argon, nitrogen or other gases. In certain embodiments, heating of mixtures to temperatures of approximately 100 to 150° C. may be effected in order to remove any residual oxygen or moisture prior to subsequent use.

Where the method of the invention is not conducted in an ionic liquid the reaction may be carried out in any convenient solvent. Protic solvents such as alcohols may be used as may aprotic solvents including chlorinated solvents (e.g. dichloromethane), hydrocarbon solvents such as hexane mixtures or toluene as appropriate, or others (e.g. ethers such as diethyl ether, tetrahydrofuran (THF), ketones such as acetone or butanone esters such as ethyl acetate). The selection of an appropriate solvent is well within the capability of a person of normal skill. Alternatively, as is known to those familiar with metathesis chemistry, it may be appropriate to conduct metathesis reactions in the absence of solvent. As with many other aspects of the method of the invention, the skilled person is well able to establish appropriate reaction conditions within his normal skill.

The method of the invention may be conducted in batch processing, i.e. in which the desired reactant(s) for the metathesis reaction is/are introduced into a suitable vessel, for example an autoclave if gaseous components (e.g. ethylene) are being used.

Alternatively, the method of the invention may be conducted on a non-batch, e.g. continuous flow basis. Such non-batch methods may be achieved by dissolving well-defined catalysts in ionic liquids, e.g. in a reactor, and introducing the substrate(s) for the metathesis reaction in supercritical carbon dioxide.

Continuous processing is described by PB Webb et al. (*J. Am. Chem Soc.*, 2003, 125, 15,577-15,588) in connection with hydroformylation of alkenes in supercritical fluid-ionic liquid biphasic systems. However, the skilled person will understand that the principles described therein as to how appropriate solubility of catalyst in ionic liquid may be achieved are applicable to the present invention. In particular, the use of appropriate salts of sulfonated phosphines is discussed in order to achieve effective solubility of catalysts in ionic liquid. The skilled person will likewise understand that the teachings by Webb et al. may be applied to sulfonated phosphites, phosphonates or phosphinates as well as phosphines, and to phosphines, phosphites, phosphonates and phosphinates bearing phosphate or carboxylate moieties, so as to maximise solubility in the ionic liquid and thereby activity of the resultant catalysts.

Another example of continuous processing, again of hydroformylation, is described by U Hintermair et al. (*Dalton Trans.*, 2010, 39, 8501-8510). In this publication, microporous silica-supported catalysts prepared from monosulfonated triphenylphosphine with an imidazolium cation and an ionic liquid are described as being used in the continuous flow hydroformylation of 1-octene in the presence of compressed carbon dioxide. In this way, continuous flow of near critical or supercritical carbon dioxide allowed continuous flow hydroformylation to be effected and it will be understood that the same principles described in this publication may also be applied to the metathesis reactions to which the present invention is directed. Reference is further made to the description of continuous flow homogeneous alkene metathesis in a similar system (see R Duque et al., *Green Chem.*, 2011, 13, 1187-1195).

It will be readily appreciated by those skilled in the art that, if desired, recognised methods of immobilisation of the catalysts described herein can be used to generate heterogeneous catalysts which retain the important features of the metathesis catalysts described herein, for example the phosphorus-coordinating ligands or catalysts may be absorbed onto a suitable solid support or reacted with such a support to form a covalently bound ligand or catalyst.

All publications (both patent and non-patent) referred to herein are hereby incorporated by reference in their entirety.

The invention may be further understood with regard to the following non-limiting clauses:

1. A method of alkene metathesis comprising contacting at least a first alkene, which comprises a carbon-carbon double bond tethered to an aromatic alcohol, with an alkylidene ruthenium alkene metathesis catalyst comprising two ligands $P^1$ and $P^2$, which may be the same or different and of formula $P(R^1)^3$, in which P is a phosphorus atom coordinated to the ruthenium ion and each $R^1$ is independently an optionally substituted alkyl or alkoxy group; or two $R^1$ groups within one $P^1$ or $P^2$ ligand constitute an optionally substituted bicycloalkyl.

2. The method of clause 1 wherein the catalyst is of formula (I):

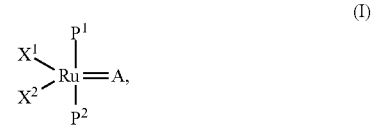

wherein:
   $P^1$ and $P^2$ are as defined in clause 1;
   $X^1$ and $X^2$ are anionic ligands, which may be the same or different; and
   A is an alkylidene group.

3. The method of clause 1 or clause 2 wherein the method is of alkene cross metathesis and the method comprises contacting the first alkene and the catalyst with a second alkene.

4. The method of clause 3 wherein the second alkene is a 1- or 2-alkene.

5. The method of clause 4 wherein the second alkene is ethylene.

6. The method of any one preceding clause wherein the first alkene comprises an internal carbon-carbon double bond.

7. The method of clause 6 wherein the aromatic alcohol is a phenol or a napthol.

8. The method of clause 6 wherein the aromatic alcohol is a phenol.

9. The method of any one preceding clause wherein the carbon-carbon double bond is tethered to the aromatic alcohol by a optionally substituted hydrocarbylene chain, which is optionally interrupted with ether, ester, amide or amine groups.

10. The method of any one preceding clause wherein the first alkene comprises a plurality of carbon-carbon double bonds.

11. The method of any one preceding clause wherein the method comprises the ethenolysis of cashew nut shell liquid, or one or more components thereof.

12. The method of any one of clauses 1 to 11 wherein the method comprises contacting ethylene with one or more compounds of formulae (II) or (III):

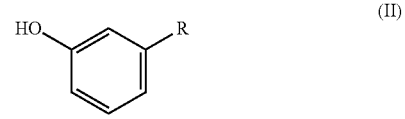

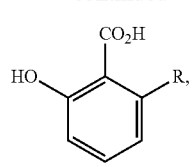

(III)

wherein —R is a hydrocarbyl chain of one of the following formulae, wherein * indicates the end of the bond through which the hydrocarbyl chain is attached to the aromatic ring:

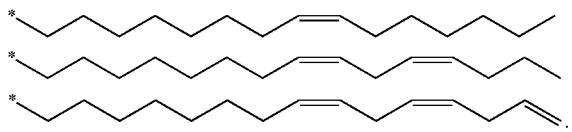

13. The method of clause 12 wherein the method comprises contacting ethylene with one or more compounds of formula (II).
14. The method of clause 12 wherein the method comprises the ethenolysis of a monoene component of cardanol.
15. The method of clause 12 or clause 13, wherein the method comprises the ethenolysis of

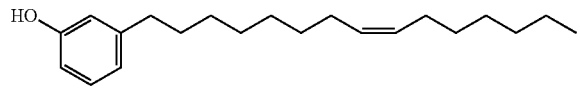

16. The method of any one of clauses 1 to 12 wherein the method is the ethenolysis of cardanol.
17. The method of any one of clauses 1 to 10 wherein the method comprises the self metathesis of a trienic component of cashew nut shell liquid.
18. The method of clause 17 wherein the trienic component is of formula (III) or formula (IV):

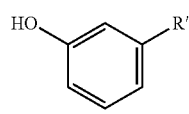

(III)

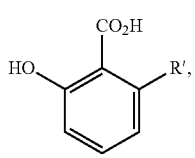

(IV)

wherein —R' is a hydrocarbyl chain of the following formula, wherein * indicates the end of the bond through which the hydrocarbyl chain is attached to the aromatic ring:

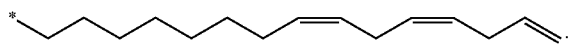

19. The method of any one of clauses 11 to 18, which is a method of preparing 3-non-8-enylphenol.

20. The method of any one of clauses 11 to 19 further comprising hydrogenating 3-non-8-enylphenol and ethoxylating the resultant 3-nonylphenol to provide ethoxy-3-nonylphenol or oligoethoxy-3-nonylphenol, in which the -oligoethoxy substituent is of formula —$(OCH_2CH_2)OH$, wherein n is an integer of between 1 and 20.
21. The method of any one of clauses 11 to 16, which is a method for preparing 1-octene.
22. The method of any one preceding clause wherein each $R^1$ is independently a branched $C_{5-10}$ alkyl, $C_{5-10}$ cycloalkyl, $C_{5-10}$ alkoxy or $C_{5-10}$ cycloalkoxy group optionally substituted once with a sulfonate, phosphate carboxylate, quaternary ammonium or PEG-containing group.
23. The method of any one preceding clause wherein each $R^1$ is unsubstituted and independently a branched $C_{5-10}$ alkyl, $C_{5-10}$ cycloalkyl, branched $C_{5-10}$ alkoxy or $C_{5-10}$ cycloalkoxy group.
24. The method of clause 22 or clause 23 wherein each $R^1$ is independently a $C_{5-10}$ cycloalkyl group.
25. The method of any one preceding clause wherein at least one of ligands $P^1$ and $P^2$ is tricyclohexylphosphine.
26. The method of any one preceding clause wherein both ligands $P^1$ and $P^2$ are the same.
27. The method of any one preceding clause wherein the alkylidene group is a moiety of formula =$CR^yR^z$ and in which one of $R^y$ and $R^z$ may be hydrogen and either or both of $R^y$ and $R^z$ may be alkyl, alkenyl, alkynyl, aryl carboxyalkyl, alkoxy, alkenyloxy, alkynyloxy or alkoxycarbonyl, or $R^y$ and $R^z$ together form a saturated, unsaturated or aromatic cyclic or bicyclic moiety.
28. The method of clause 27 wherein $R^y$ is hydrogen, alkyl or aryl and $R^z$ is alkyl, alkenyl or aryl
29. The method of clause 27 wherein the alkylidene group is optionally substituted indenylidene.
30. The method of clause 29 wherein the alkylidene group is a phenyl-substituted indenylidene.
31. The method of clause 29 wherein the alkylidene group is 3-phenyl-1H-inden-1-ylidene.
32. The method of clause 31 wherein the catalyst is a dihalo(3-phenyl-1H-inden-1-ylidene)bis(tricyclohexylphosphine) ruthenium (II).
33. The method of clause 32 wherein the catalyst is a dichloro(3-phenyl-1H-inden-1-ylidene)bis(tricyclohexylphosphine) ruthenium (II).
34. An alkene obtained or obtainable by the method of any one preceding clause.

The invention is further illustrated by the following non-limiting examples below:

General

All reagents were purchased from Sigma-Aldrich and used as received. All solvents were purchased from Sigma-Aldrich and were purified, dried and stored under nitrogen atmosphere in Schlenk tubes prior to being used. The following catalysts were used:

M1
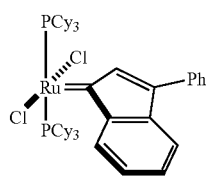

M1(ph)
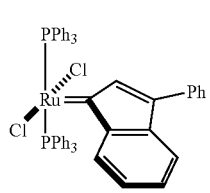

M20
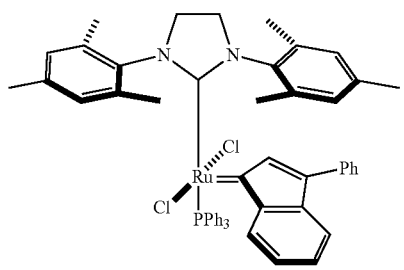

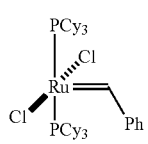
Grubbs Catalyst 1st generation

M2
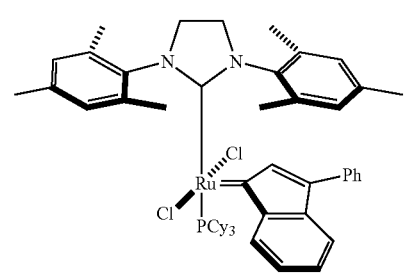

Caz-1
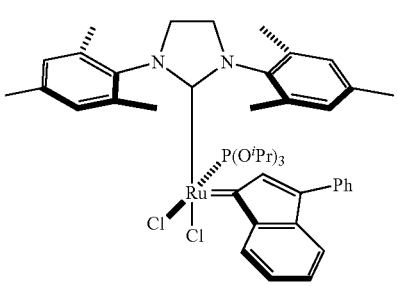

M31
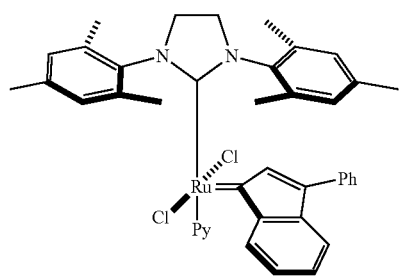

These were obtained from Umicore, Germany and/or Aldrich, or provided by Dr Catherine Cazin (University St Andrews) and were stored in a glove box. CNSL was extracted from shells collected from coastal Region, (Kibaha) Tanzania. Anacardic acid was obtained from the oil by a literature method (R. Paramashivappa et al., *J. Agric. Food Chem.*, 2001, 49, 2548-2551) and cardanol was obtained by decarboxylation of anacardic acid. Cardanol was vacuum dried-before it was subjected to reactions. The double bond composition in cardanol was determined by an NMR method involving integration of the protons from terminal double bonds, methylene H atoms between double bonds, internal double bonds and aromatic protons.

Instrumentation and preparation of cardanol are as described in J A Mmongoyo et al. (infra)

Procedure

For the ethenolysis of cardanol the crude cardanol mixture was purified via column chromatography with silica and pentane/diethylether (1:1) as eluent. Dichloromethane was dried and degassed prior use. The reaction was carried out under nitrogen. The cardanol used in these studies had the following composition (cf Table 1):

| Component | Weight Percentage |
| --- | --- |
| Triene | 28.9 |
| Diene | 18.3 |
| Monoene | 52.6 |
| Saturated | 1.1 |

Scheme 1 shows, with the percentage of each component on the left, the main products resultant from the ethenolysis of this composition of cardanol, 3-non-8-enylphenol (A) and 1-octene being the desired products:

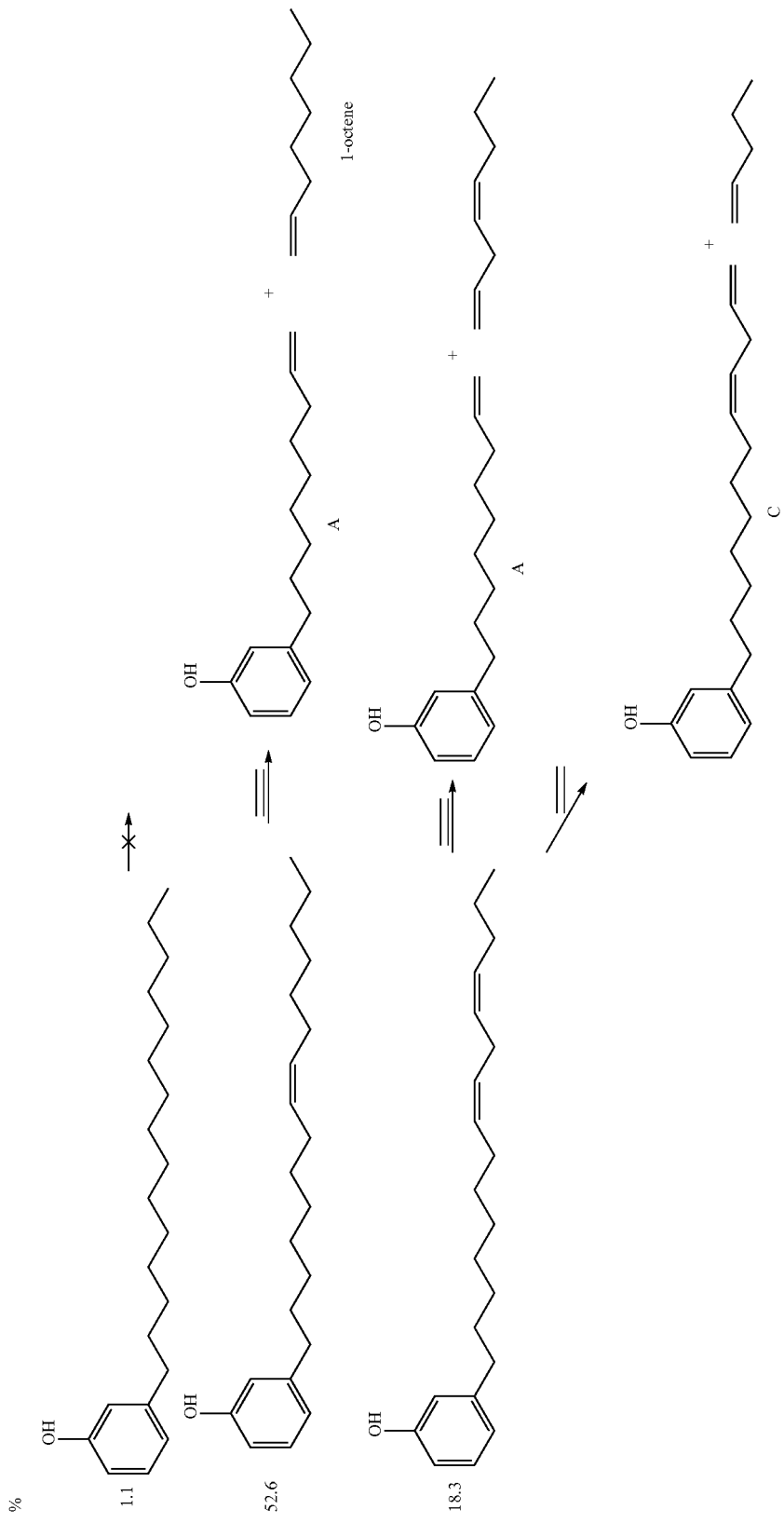

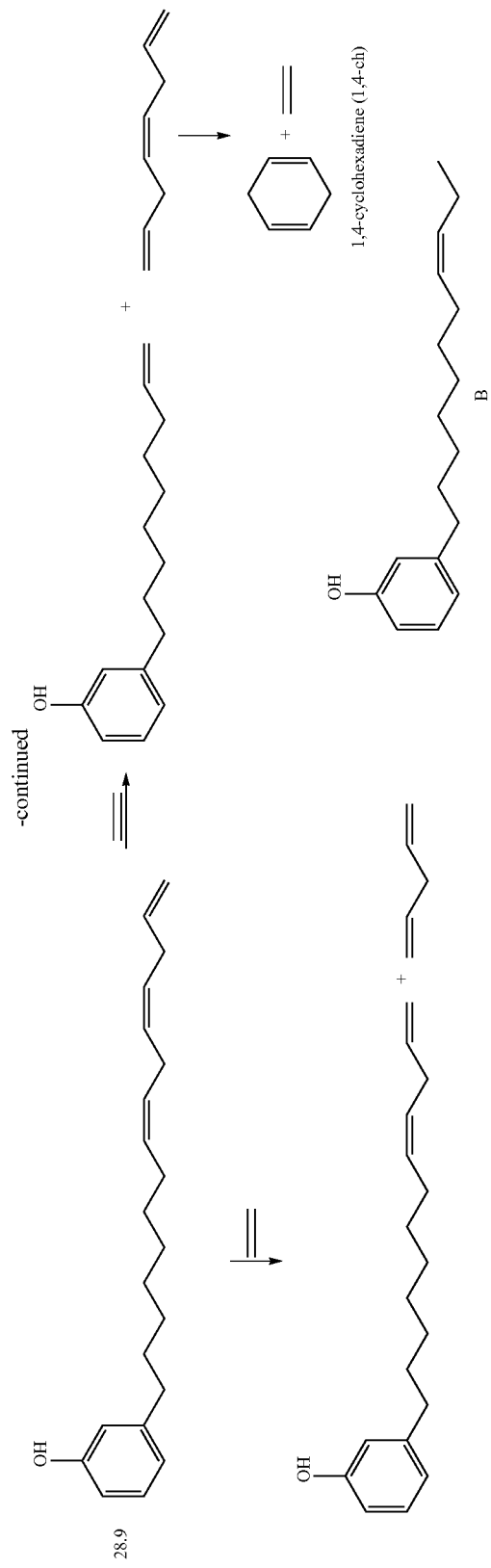

Secondary products can be obtained by metathesis of 1-octene with itself, octadiene or C5 compounds; or from cardanol with itself or with the alkenes. These secondary products are referred to as "Others" in Tables 2-4 below apart from compound B, the origin of which is not completely clear.

Catalyst (0.5 mg, 0.5 μmol) was weighed in the glove box and dissolved in dichloromethane (0.5 mL). The solution was transferred into a high-pressure reactor and, after adding cardanol (294.4 mg, 0.98 mmol) and dichloromethane (1.7 mL), the reaction mixture was pressurised with ethene (8 bar). The solution was heated to the desired temperature and stirred for 6 h.

The reactor was slowly depressurised and the reaction quenched by adding ethylvinylether (0.5 mL). The reaction mixture was analysed via GC analysis with n-tetradecane as internal standard.

The results are presented as percentages of cardanol that were converted to the different products. Thus, if 50% the cardanol were converted to A and 1-octene only, the conversion would be 50%, with selectivities to cardanol of 100% and to 1-octene of 100%.

Calculations assume that all the phenolic products are accounted for by signals in the GCMS. The amounts of 1-octene and 1,4-cyclohexadiene (1,4-ch) are determined from the amount of A using response factors determined from calibration curves. In some cases, heavier products were formed. These have not been included in the calculation so that in these case the amounts of A, B, C and "Others" are overestimated so that the amounts of 1-octene and 1,4-ch are overestimated and can add to >100%.

Results

The results of the various experiments using the different catalysts are shown in Tables 2-4.

TABLE 2

Products from ethenolysis reactions carried out at 20° C.

| Entry | catalyst | Conversion [%] | Selectivity [%] | | | | | |
|---|---|---|---|---|---|---|---|---|
| | | | A[1] | B[1] | C[1] | others[1] | octene[2] | 1,4-ch[2] |
| 1 | M1 | 96.1 | 93.3 | 3.8 | 1.4 | 1.5 | 40.7 | 30.7 |
| 2 | M20 | 26.3 | 41.8 | 1.8 | 24.9 | 30.5 | 54.2 | 70.2[3] |
| 3 | M2 | 56.8 | 19.2 | 1.4 | 14.1 | 65.3 | 75.0 | 50.3[3] |
| 4 | Caz-1 | Not attempted | — | — | — | — | — | — |
| 5 | M31 | 67.3 | 45.9 | 2.4 | 23.8 | 27.9 | 22.0 | 57.1 |
| 6 | M1(Ph) | 5.7 | 0.0 | 0.0 | 0.0 | >99 | 0.0 | 0.0 |
| 7[3] | HG2 | 85.7 | 26.3 | 0.9 | 0.0 | 72.8 | 21.3 | 63.6 |

6 h, 8 bar C$_2$H$_4$, 20° C., cat/sub: 1/1800, c(cardanol) = 0.4 mol/L, conversion and selectivities determined via GC analysis
[1]selectivity is related to phenolic compounds formed in the ethenolsyis;
[2]selectivity is related to olefinic products, which are formed as co-products in the ethenolysis;
[3]octane and cyclohexadiene together are higher than 100% due to oligomerisation products of cardanol, which couldn't be integrated in the GC, therefore the conversion in these cases is lower then indicated in the table;
[4]24 h, 20 bar C$_2$H$_4$, cat/sub: 1:330, c(cardanol) = 0.44 mol/L. Different cardanol batch.

TABLE 3

Products from ethenolysis reactions carried out at 40° C.

| Entry | catalyst | Conversion [%] | Selectivity [%] | | | | | |
|---|---|---|---|---|---|---|---|---|
| | | | A[1] | B[1] | C[1] | others[1] | octene[2] | 1,4-ch[2] |
| 1 | M1 | 94.8 | 93.5 | 3.2 | 2.3 | 1.1 | 38.8 | 28.2 |
| 2 | M20 | 82.7 | 53.9 | 2.3 | 19.5 | 24.3 | 24.6 | 35.3 |
| 3 | M2 | 60.6 | 33.9 | 2.0 | 12.0 | 52.1 | 94.0 | 61.2[3] |
| 4 | Caz-1 | 61.2 | 8.6 | 0 | 16.6 | 74.8 | 76.2 | 53.3[3] |
| 5 | M31 | 83.1 | 52.5 | 2.7 | 19.4 | 25.4 | 21.3 | 46.2 |
| 6 | M1(Ph) | 5.2 | 0.0 | 0.0 | 0.0 | >99 | 0.0 | 0.0 |

6 h, 8 bar C$_2$H$_4$, 40° C., cat/sub: 1/1800, c(cardanol) = 0.4 mol/L, conversion and selectivities determined via GC analysis;
[1]selectivity is related to phenolic compounds formed in the ethenolsyis;
[2]selectivity is related to olefinic products, which are formed as co-products in the ethenolysis;
[3]octane and cyclohexadiene together are higher than 100% due to oligomerisation products of cardanol, which couldn't be integrated in the GC, therefore the conversion in these cases is lower then indicated in the table;.

TABLE 4

Products from ethenolysis reactions carried out at 70° C.

| Entry | catalyst | Conversion [%] | Selectivity [%] | | | | | |
|---|---|---|---|---|---|---|---|---|
| | | | A[1] | B[1] | C[1] | others[1] | octene[2] | 1,4-CH[2] |
| 1 | M1 | Not attempted | — | — | — | — | — | — |
| 2 | M20 | 86.6 | 48.5 | 2.2 | 14.9 | 34.4 | 24.6 | 26.7 |
| 3 | M2 | 83.5 | 67.9 | 2.9 | 12.2 | 17.0 | 94.0[3] | 29.8[3] |
| 4 | Caz-1 | 57.8 | 21.5 | 6.6 | 13.8 | 58.1 | 76.2[3] | 28.7[3] |
| 5 | M31 | 86.6 | 58.9 | 3.0 | 21.5 | 16.6 | 21.3 | 42.7 |
| 6 | M1(Ph) | 12.0 | 0.0 | 0.0 | 0.0 | >99 | 0.0 | — |

6 h, 8 bar C$_2$H$_4$, 70° C., cat/sub: 1/1800, c(cardanol) = 0.4 mol/L, conversion and selectivities determined via GC analysis;
[1]selectivity is related to phenolic compounds formed in the ethenolsyis;
[2]selectivity is related to olefinic products, which are formed as co-products in the ethenolysis;
[3]octane and cyclohexadiene together are higher than 100% due to oligomerisation products of cardanol, which couldn't be integrated in the GC, therefore the conversion in these cases is lower then indicated in the table.

The invention claimed is:

1. A method of preparing 3-non-8-enylphenol by ethenolysis comprising:
    contacting at least a first alkene, which is cardanol, with an alkylidene ruthenium alkene metathesis catalyst according to formula (I):

(I)

wherein: ligands $P^1$ and $P^2$ may be the same or different and of formula $P(R^1)_3$, in which P is a phosphorus atom coordinated to the ruthenium ion and each $R^1$ is independently a $C_{5-10}$ cycloalkyl group; $X^1$ and $X^2$ are anionic ligands, which may be the same or different; and A is an alkylidene group.

2. The method of claim 1 wherein the method comprises the ethenolysis of cashew nut shell liquid.

3. The method of claims 1 wherein the method comprises the self metathesis of a trienic component of cashew nut shell liquid.

4. The method of claim 3 wherein the trienic component is of formula (III):

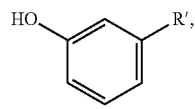

wherein —R' is a hydrocarbyl chain of the following formula, wherein * indicates the end of the bond through which the hydrocarbyl chain is attached to the aromatic ring:

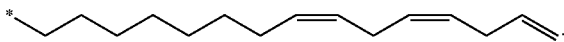

5. A method of preparing ethoxy-3-nonylphenol or oligoethoxy-3-nonylphenol from the 3-non-8-enylphenol produced in claim 1 further comprising hydrogenating the 3-non-8-enylphenol and ethoxylating the resultant 3-nonylphenol to provide ethoxy-3-nonylphenol or oligoethoxy-3-nonylphenol, in which the -oligoethoxy substituent is of formula (OCH2CH2)nOH, wherein n is an integer of between 1 and 20.

6. The method of claim 1 wherein at least one of ligands $P^1$ and $P^2$ is tricyclohexylphosphine.

7. The method of claim 1 wherein both ligands $P^1$ and $P^2$ are the same.

8. The method of claim 1 wherein the alkylidene group is a moiety of formula $=CR^yR^z$ and in which one of $R^y$ and $R^z$ may be hydrogen and either or both of Ry and Rz may be alkyl, alkenyl, alkynyl, aryl carboxyalkyl, alkoxy, alkenyloxy, alkynyloxy or alkoxycarbonyl, or $R^y$ and $R^z$ together form a saturated, unsaturated or aromatic cyclic or bicyclic moiety.

9. The method of claim 8 wherein $R^y$ is hydrogen, alkyl or aryl and $R^z$ is alkyl, alkenyl or aryl.

10. The method of claim 8 wherein the alkylidene group is optionally substituted indenylidene.

11. The method of claim 10 wherein the alkylidene group is a phenyl-substituted indenylidene.

12. The method of claim 10 wherein the alkylidene group is 3-phenyl-1H-inden-1-ylidene.

13. The method of claim 12 wherein the catalyst is a dihalo(3-phenyl-1H-inden-1-ylidene)bis(tricyclohexylphosphine) ruthenium (II).

14. The method of claim 13 wherein the catalyst is a dichloro(3-phenyl-1H-inden-1-ylidene)bis(tricyclohexylphosphine) ruthenium (II).

* * * * *